United States Patent [19]

Hayes

[11] Patent Number: 5,094,944
[45] Date of Patent: Mar. 10, 1992

[54] FLOURESCENT AQUATIC BIOASSAY AND PROCEDURE

[76] Inventor: Kenneth R. Hayes, P.O. Box 216, Sergeantsville, N.J. 08557

[21] Appl. No.: 503,296

[22] Filed: Apr. 2, 1990

Related U.S. Application Data

[63] Continuation-in-part of Ser. No. 343,360, Apr. 26, 1989, abandoned.

[51] Int. Cl.$^5$ ................................................ C12Q 1/04
[52] U.S. Cl. .......................................... 435/29; 424/9; 435/31; 435/34; 435/4
[58] Field of Search .................. 435/29, 31, 34; 424/9

[56] References Cited

U.S. PATENT DOCUMENTS 4,534,317 8/1985 Walsh .
4,774,173 9/1988 Reinhartz .............................. 435/5
4,812,409 3/1989 Babb et al. .

OTHER PUBLICATIONS

Zhao et al., Chem. Abst., vol. 105, (1986), p. 220,314g.
Obst and Wigand-Rosinus, in "Application of Enzyme Assays for Toxicological Water Testing", Toxicity Assessment: An International Journal, vol. 3, 81 (1988).
Holzapfel-Psorn, et al., in "Sensitive Methods for the Determination of Microbial Activities in Water Samples Using Fluorigenic Substrates", Fresenius Z. Anal. Chem., 327, 521 (1987).
Obst, in "Test Instructions for Measuring the Microbial Metabolic Acitvity in Water Samples", Fresenius Z. Anal. Chem., 321, 166 (1985).
Kaiser and Ribo, in "Photobacterium Phosphoreum Toxicity Bioassay. II. Toxicity Data Compilation", Toxicity Assessment: An International Journal, vol. 3, 195 (1988).
Querishi, et al., in "Comparison of a Luminescent Bacterial Test with Other Bioassays for Determining Toxicity of Pure Compounds and Complex Effluents", Aquatic Toxicology: Fifth Conference.
Ribo and Kaiser, in "Photobacterium Phosphoreum Toxicity Bioassay I. Test Procedures and Applications", Toxicity Assessment: An International Quarterly, vol. 2, 305 (1987).
Curtis, et al., in "Evaluation of a Bacterial Bioluminescence Bioassay as a Method for Predicting Acute Toxicity of Organic Chemicals to Fish", in Aquatic Toxicology: Fifth Conference.
Tarkpea and Hansson, in "Comparison Between Two Microtox Test Procedures", Ecotoxicology and Environmental Safety, 18, 204 (1989).
Schmitt-Biegel and Obst, "Rationelle Fluorimetrishce Bestimmung von Enzymaktivitaten in vivo unter der Biomasse (DNA) auf Mikrotiterplatten", in Z. Wasser-Abwasser-Forsch, 22, 165–167 (1989).
Holzapfel-Pschorn et al., in "Einsatz enzymatischer Untersuchungen in der Wasseraufbereitung", Fresenius Z. Anal. Chem., 330, 439 (1988).
Hoppe, in "Significance of Exoenzymatic Activities in the Ecology of Brackish Water: Measurements by Means of Methylumbelliferylsubstrates", Mar. Ecol. Prog. Ser., 11, 299 (1983).
Schnurer and Rosswall, in "Fluorescein Diacetate Hydrolysis as a Measure of Total Microbial Activity in Soil and Litter", Applied and Environmental Microbiology, Jun., 1982, pp. 1256–1261.
Sundt, Jr. and Anderson, in "Umbelliferone as an Intracellular pH-Sensitive Fluorescent Indicator and Blood-Brain Barrier Probe: Instrumentation, Calibration, and Analysis".

(List continued on next page.)

Primary Examiner—Sam Rosen
Attorney, Agent, or Firm—Henry D. Coleman; R. Neil Sudol

[57] ABSTRACT

The present invention relates to a novel assay for determining levels of toxicants in aqueous environments, preferably in water supplies. The present invention also relates to a method for utilizing the assay to test the level of toxicants in an aquatic source. Further embodiments of the present invention relate to a test kit embodying the assay of the present invention. More specifically the assay involves the use of enzyme substrates having an umbelliferyl group and multi-cellular organisms having bodies which fluoresce.

20 Claims, 4 Drawing Sheets

OTHER PUBLICATIONS

Teuber and Brodisch, in "Enzymatic Activities of Activated Sludge", *European J. Appl. Microbiol.*, 4, 185, (1977).

Flint and Hopton, in "Substrate Specificity and Ion Inhibition of Bacterial and Particle Associated Alkaline Phosphatases of Waters and Sewage Sludges", *European J. Appl. Microbiol.*, 4, 195, (1977).

Burton, in "Evaluation of Seven Sediment Toxicity Tests and Their Relationships to Stream Parameters", *Toxicity Assessment: An International Journal*, 4, 149 (1989).

Burton and Stemmer, in "Evaluation of Surrogate Tests in Toxicant Impact Assessments", *Toxicity Assessment: An International Journal*, vol. 3, 255 (1988).

Burton et al.., in "A Multitrophic Level Evalution of Sediment Toxicity in Waukegan and Indiana Harbors", *Environmental Toxicology and Chemistry*, 8, 1057 (1989).

Dutton et al., "Application of a Direct Microscopic Method of the Determination of Active Bacteria, in Lakes", *Wat. Res.*, 20, 1461 (1986).

Burton and Lanza, in "Sediment Microbial Activity Tests for the Detection of Toxicant Impacts", Aquatic Toxicology and Hazard Assessment: Seventh Symposium, 214–228 (1985).

Burton and Lanza, in "Aquatic Microbial Activity and Macerofaunal Profile of an Oklahoma Stream", *Wat. Res.*, vol. 21, 1173 (1987).

Cloete and Steyn, in "The Role of Acinetobacter as a Phosphorus-Removing Agent in Activated Sludge", *Wat. Res.*, 22, 971 (1988).

Olah and Princz, *Wat. Res.*, 20, 1529 (1986).

Cloete and Steyn, *Wat. Res.*, 22, 961 (1988).

Katayama-Hirayama, *Wat. Res.*, 20, 491 (1986).

Tan, *Marine Biology*, 76, 247 (1983).

Alsop et al, *Journal WPCF*, 52, 2452 (Oct. 1980).

McPeters et al., *Wat. Res.*, 12, 1757 (1983).

Dutka et al., *Wat. Res.*, 17, 1363 (1983).

Vives-Rego et al., *Wat. Res.*, 20, 1411 (1986).

Robinson, *Toxicity Assessment: An International Journal*, vol. 3, 17 (1988).

Sogawa and Takahashi, *J. Biochem*, 83, 1783 (1978).

Owens and King, *Marine Biology*, 30, 27 (1975).

Pandya et al., *Wat. Res.*, 22, 1055 (1988).

Roth, p. 257, "Fluorimetric Assay of Enzymes".

Hestrin, pp. 225–226, *Biochemist's Handbook*, Van Nostrand 1961, Cecil Long, Ed.

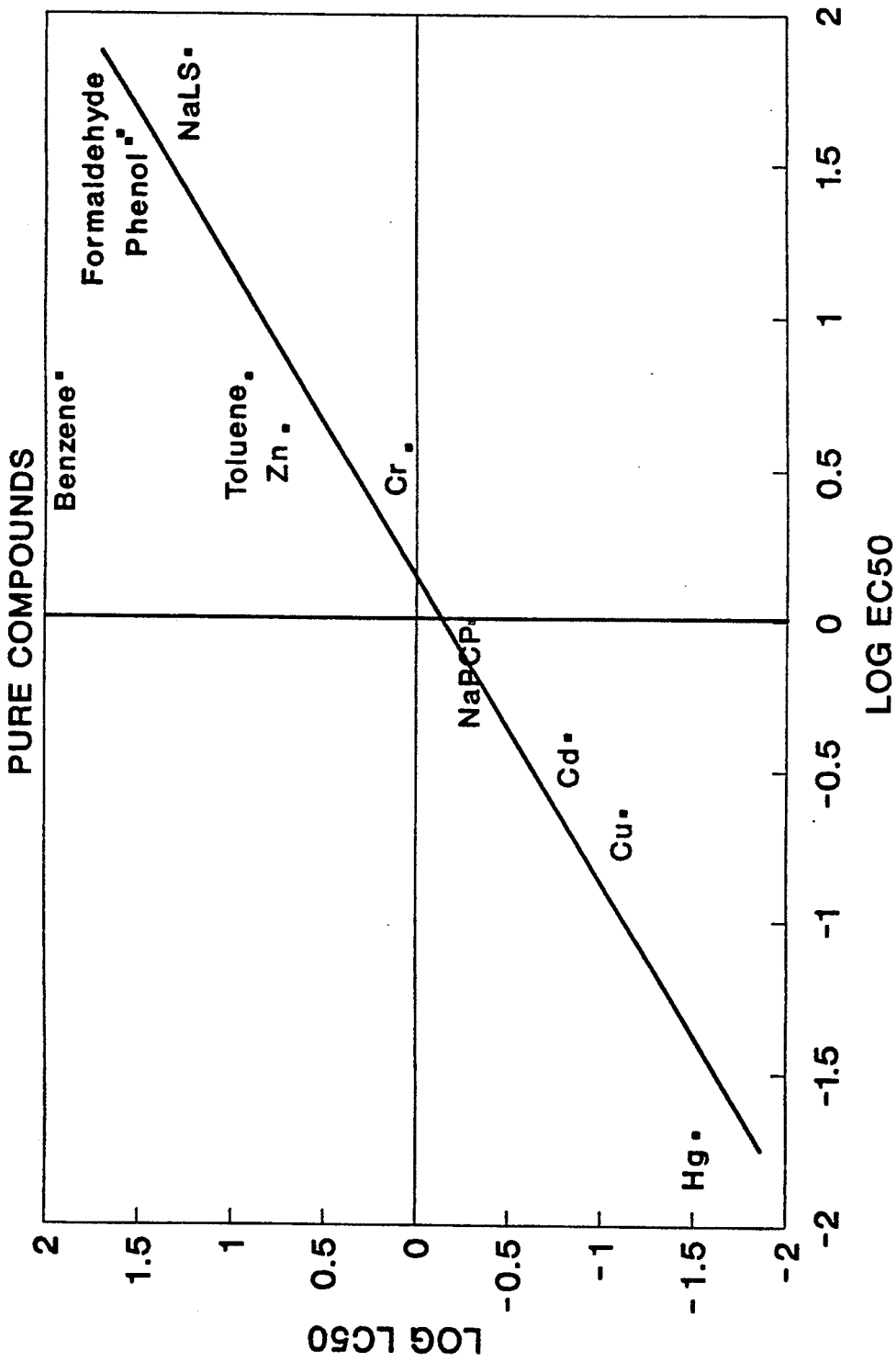

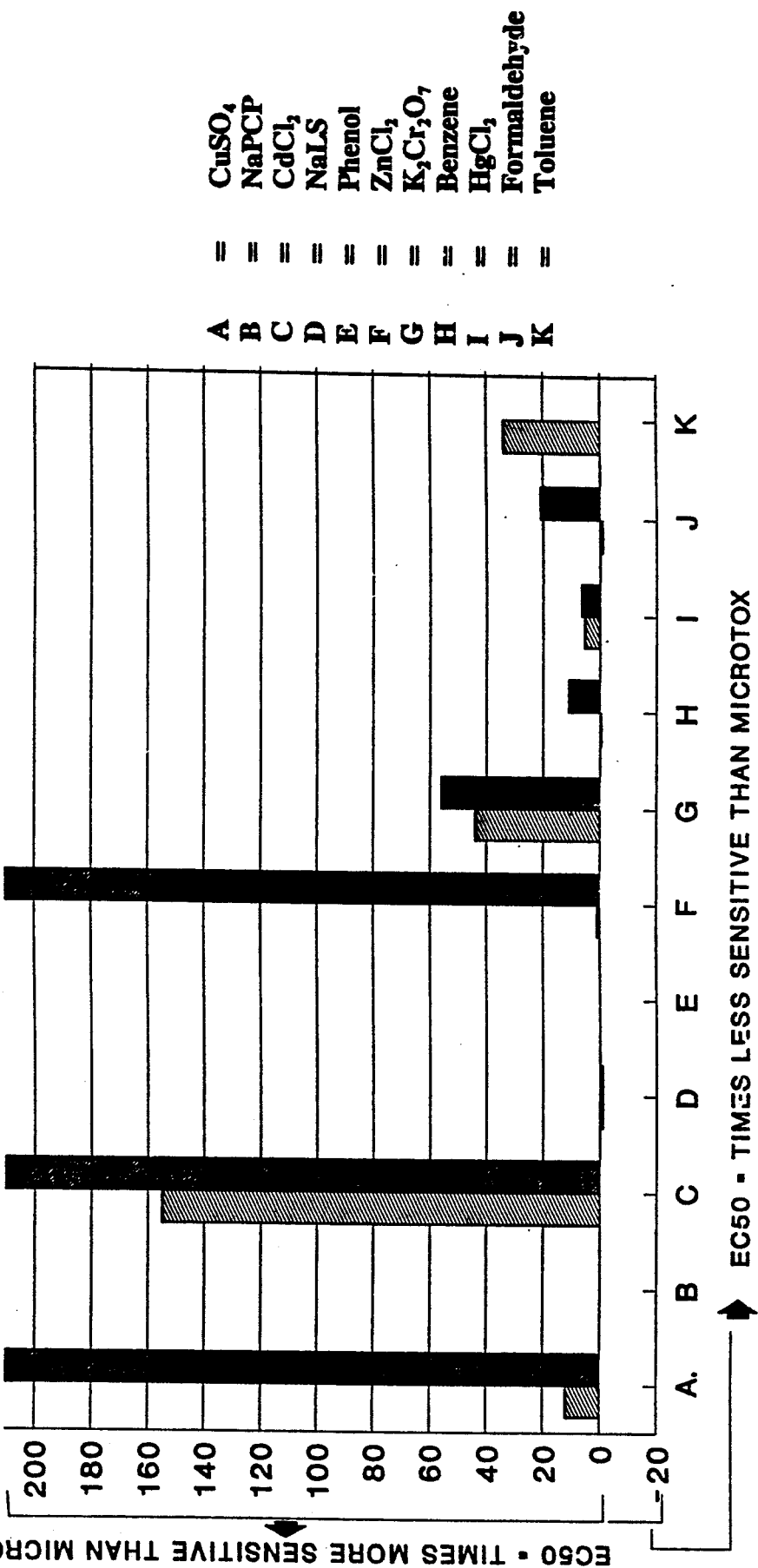

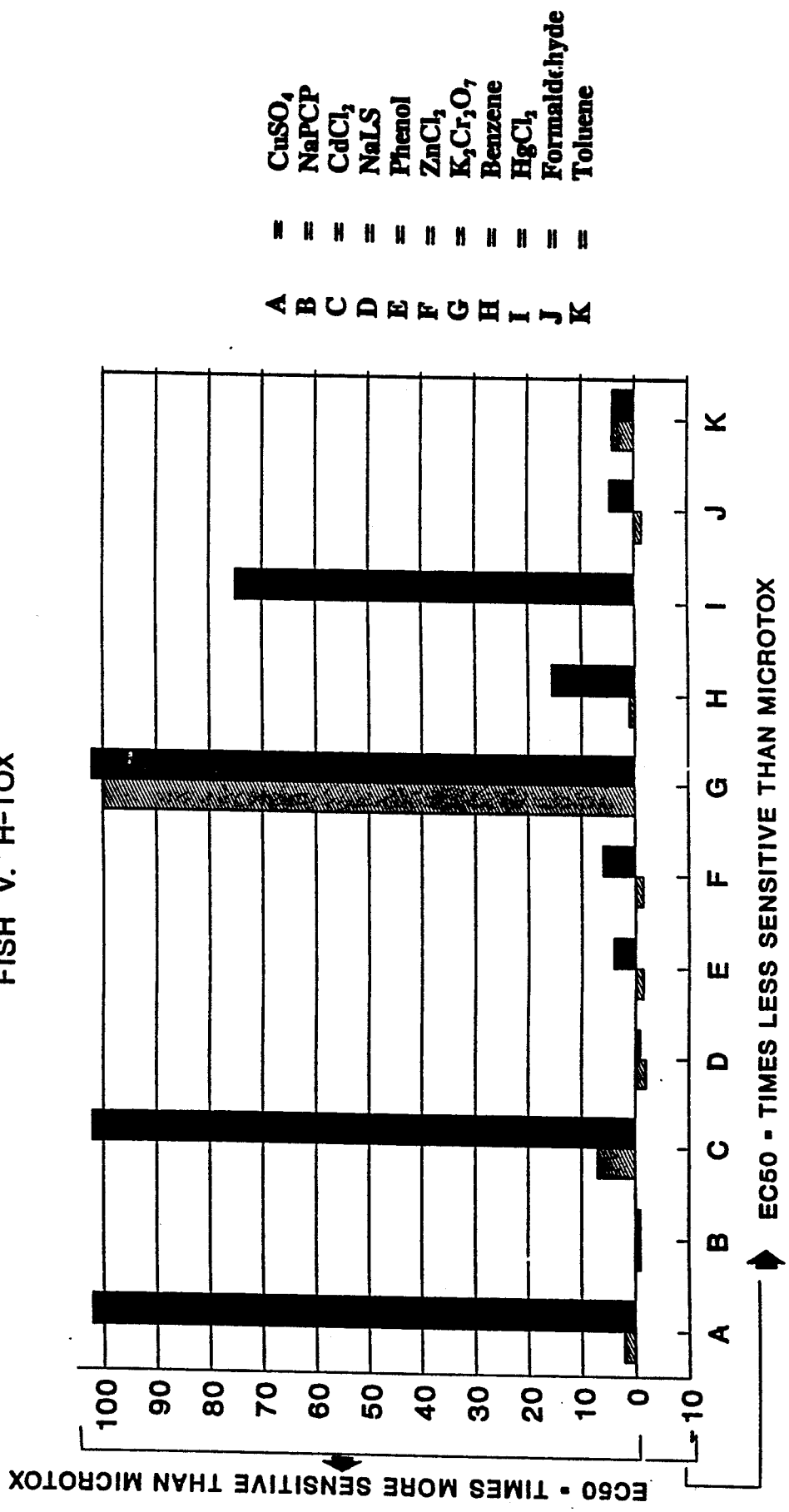

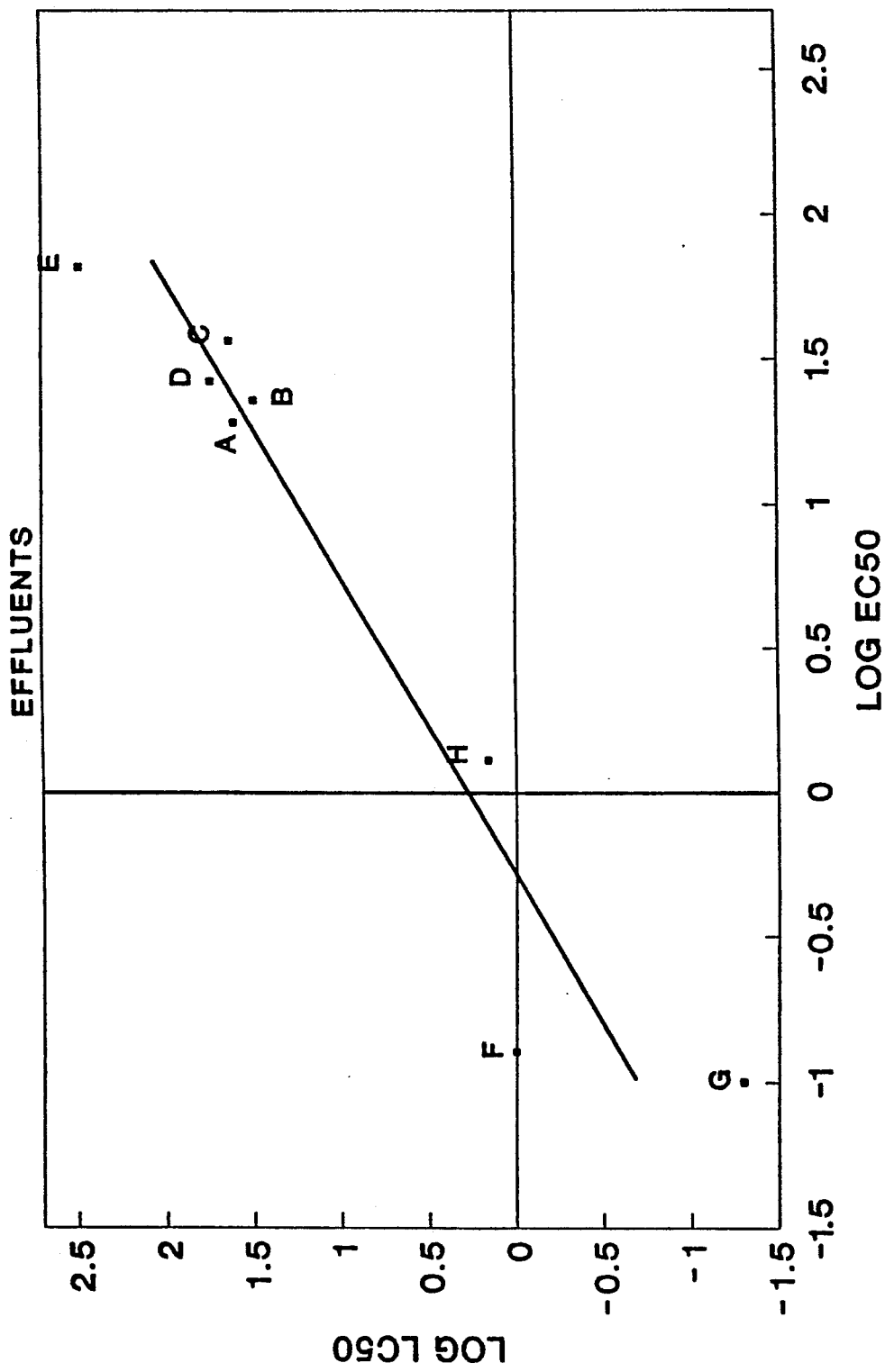

FLOURESCENT AQUATIC BIOASSAY AND PROCEDURE

This patent application is a continuation-in-part application of U.S. Ser. No. 343,360 entitled, "Fluorescent Aquatic Bioassay Procedures", filed Apr. 26, 1989, now abandoned,

FIELD OF THE INVENTION

The present invention relates to an aquatic environmental toxicology assay employing fluorescent markers, a method of using this novel assay and a kit for use in aquatic analysis.

BACKGROUND OF THE INVENTION

There are a number of enzymatic activity tests which have used spectrophotometric or fluoremetric methods to enumerate active and inactive microbes [See, for example, Flint, *European J. Appl. Microbiol.*, 4, 195 (1977); Dutton, et al., *Wat. Res.*, 20, 1461 (1986); Burton, et al., *Wat. Res.*, 21, 1173 (1987); "Sediment Microbial Activity Tests for the Detection of Toxicant Impacts" *Aquatic Toxicology: Seventh Symposium*, ASTM STP R. D. Caldwell, et al., Ed. American Society for Testing and Materials, Philadelphia, 1985 pp. 214-228; *Environmental Toxicology and Chemistry*, 8, 1057 (1989); *Toxicity Assessment*, 4, 149 (1989); *Toxicity Assessment*, 4, 255 (1989); Cloete, et al., *Wat. Res.*, 22, 961 (1988); *Wat. Res.*, 22, 971 (1988); Katayama-Hirayama, *Wat. Res.*, 20, 491 (1986); Obst, *Fresnius Z. Anal. Chem* 321, 166, (1985); Obst, et al., *Toxicity Assessment*, 3, 81 (1988)]; and to determine active biomass [See, for example, Teuber, et al., *European J. Appl. Microbiol.*, 4, 185 (1977); Schnurer, *Applied and Environmental Microbiology*, 43, 1256 (1982); Hoppe, *Mar. Ecol. Prog. Ser.*, II, 299 (1983); and Tan, *Marine Biology*. 76, 247 (1983).

Fluorescent indicators have been utilized in cats and rats to measure central nervous system pH [See, for example, Sundt, et al., "*Umbelliferone as an Intracellular pH-Sensitive Fluorescent Indicator and Blood-Brain Barrier Probe: Instrumentation, Calibration and Analysis*", 60 (1980)]. U.S. Pat. No. 4,534,317 discloses fluorescing dyes which are used to monitor fish food consumption.

None of the methodologies disclosed in the art utilizes a series of test concentrations to develop standard LC50 and EC50 toxicity values that are required by the *Federal Water Pollution Control Act Amendments (Clean Water Act) of 1977 (PL 95-217). Section 101(a)(3)*. Nor do any of these methodologies provide a measure of toxicants in an aquatic body in a fast and efficient manner.

The present preferred method for determining aquatic toxicity in water supplies generally utilizes a 48 hour daphnia test or a 96 hour fathead minnow test. In these methodologies, the multicellular organisms are exposed to a toxicant for a period of 2 to 4 days and then the live organisms are counted to determine death rate. Other bioassay tests, which utilize 24 hour to 21-day tests, are described by the United States Environmental mental Protection Agency, ASTM, SETAC, OECD and various other State and private research groups. There is a clear need in the art for a fast, easy to use bioassay test which has reliability and accuracy, and which may be used with confidence by a lay person.

It is an object of the present invention to provide an aquatic bioassay that can be used to measure various toxicants in aquatic sources in an easy, fast and efficient manner.

It is a further object of the present invention to provide a novel aquatic bioassay which ca test both lethal (acute) and sublethal (chornic) concentrations of toxicants in aquatic sources.

It is still an additional object of the present invention to provide a method for determining the concentrations of various toxicants in aquatic sources in a fast, efficient manner.

It is still another object of the present invention to provide a bioassay kit for testing toxicants in aquatic sources.

These and other objects of the present invention may be readily determined by a review of the description and the examples of the present invention.

SUMMARY OF THE INVENTION

The present invention relates to a novel assay for determining levels and effects of toxicants in aqueous environments, preferably in water supplies. The present invention also relates to a method for utilizing the assay to test the level of toxicants in an aquatic source. Further embodiments of the present invention relate to a test kit embodying the assay of the present invention.

In a first aspect, the present invention relates to an aquatic bioassay for determining the existence of toxicants in an aquatic source comprising:
 a) at least one test sample comprising:
  i. an aquatic source containing a toxicant to be tested;
  ii. an effective amount of an enzyme substrate which results in a fluorescent product after enzymatic modification; and
  iii. a concentration of a living organism having an enzyme system capable of enzymatically modifying said enzyme substrate to produce said fluorescent product in an amount sufficient to be fluorescently identified; and
 b) reference standards, at least one of said reference standards comprising:
  i. an aquatic source containing a known toxicant concentration;
  ii. an identical amount of said enzyme substrate from (a)ii; and
  identical concentration of said living organism from (a)iii);
  and a second reference standard comprising;
  i. an aquatic source containing an absence of toxicant;
  ii. an identical amount of said enzyme substrate from (a)ii; and
  iii. an identical concentration of said living organism from (a)iii).

In addition, the above bioassay preferably contains at least three reference standards, each reference standard containing different concentrations of toxicant.

In the bioassay of the present invention, any aquatic source may be analyzed to determine the concentration or effect of toxicants. Sources of media from reservoirs, rivers, lakes, streams, ponds and other bodies of water, industrial wastestreams, municipal wastestreams, leachate, elutriate, liquid phase, suspended particulate phase, point and non-point source samples and pure compounds, and aqueous environments, including salt water aquatic sources may be tested to determine the levels and effects of toxicants for purposes of meeting water safety guidelines, to determine the safety of drinking water and for determining the effect of toxicants on the microorganisms in sludge at waste treatment centers, among other uses.

The bioassay of the present invention utilizes a test sample containing a water source to be analyzed for a toxicant or toxicants and several reference samples, each reference sample containing an amount of a toxicant which is different from another reference source. All the samples, including the test sample and reference samples, preferably contain substantially identical concentrations of enzyme substrate and numbers of living organisms. In general, each test sample and reference sample is preferably analyzed in triplicate.

In the method of the present invention, a test sample is prepared by measuring out an aqueous test sample and placing a number of living organisms into the test sample. After an elapsed time period, a measured amount of enzyme substrate is added to each concentration. This concentration of enzyme substrate and number of living organisms is sufficient to allow enzymatic modification of the enzyme substrate into a fluorescent product which may be identified using standard fluorometric techniques. In addition to the test sample, several reference standards can be prepared (preferably, each in triplicate). Each reference standard contains a known concentration of toxicant which may range from zero to rather high concentrations. Each reference sample also contains a concentration of enzyme substrate and living organisms identical to that of the test sample.

After preparation of the test sample(s) and the reference standards, the enzyme substrate in a reference solvent, preferably distilled water, is sonicated for a short period of time (generally, about 30 seconds to several minutes) and added to the test sample(s) and reference standards, which are then incubated for a period of time sufficient to allow enzymatic modification of the enzyme substrate into a fluorescent product. This period of incubation generally ranges from about a minute to about several hours. Generally, the incubation temperature will depend upon the species of living organism used in the bioassay and the kinetics of the enzyme performing the modification of substrate. However, in general, the test samples and reference samples are incubated at a temperature ranging from about 0° C. to about 25° C., although higher and lower temperatures may be used. After allowing incubation for a period of time sufficient to enable the enzyme to modify the enzyme substrate, each sample is measured for fluorescence by exposing the chambers to an ultraviolet (UV) light source and then observing the fluorescence visually or alternatively with a fluorometer. After the fluorescence of each sample is determined, the fluorescence of the test sample is compared with the fluorescence of the reference standards. This may be done by simple visualization or alternatively with instrumentation, such as a fluorometer (Sequoia-Turno Model #450, Farrand Mark Spectrofluorometer or Gilford Fluoro IV Scanning Spectrofluorometer).

By comparing the intensity of the fluroescence of the test sample with the reference standards, the amount of toxicant and/or the toxic effect of the tested aquatic source can be determined. Using this procedure the concentration of one or more toxicants may be measured. In addition, standard $LC_{50}$ and $EC_{50}$ toxicity values for a broad range of toxicants may be easily predicted and/or determined.

The present invention also relates to a test kit comprising an enzyme substrate in an amount sufficient to produce a final concentration of about 1 ppm to about 100 ppm and directions for using the enzyme substrate. In certain kits, live (including encysted) organisms in numbers sufficient to produce fluorescent product in a measurable amount may also be included. In addition to enzyme substrate or substrate and live organisms the kit of the present invention may also contain any one or more of the following: exposure chambers such as a multiwell plate or test tubes, distilled water, pipettes (test media and diluent media), substrate mixing vial, sonicator, directions, black light (UV source), fluorometer, UV safety glasses or goggles, a light box, an autopipettor, safety gloves, score card, statistical programs, associated packaging, a black box and combinations of these components.

BRIEF DESCRIPTION OF THE FIGURES

FIG. 1 is a graphic representation of the $EC_{50}$ values of Example 2 correlated to 48 hour LC50 values.

FIG. 2 compares data generated from Example 2 with Microtox high and low $EC_{50}$ pure compound values taken from the literature. In almost every case, the present invention was as sensitive as or more sensitive than the Microtox tests.

FIG. 3 compares data generated from Example 2 with 96 hour $LC_{50}$ pure compound values taken from the literature for *Pimephales promelas* (fathead minnow). In this comparison, the present invention was as sensitive as or more sensitive than the fathead minnow test.

FIG. 4 compares data generated when several complex effluents were bioassayed with conventional 48 hour $LC_{50}$ methodology and the present invention. The results produced an excellent correlation ($R^2$ values ranged from 0.90 to 0.96). In this figure, the $EC_{50}$ and $LC_{50}$ values are expressed in percent effluent.

DETAILED DESCRIPTION OF THE INVENTION

The following definitions are used throughout the specifiction to describe the present invention.

The term "toxicant" is used throughout the specification to describe any toxic substance in a water supply which may have a deleterious effect on a biological system and includes chemical compositions, macromolecules, biochemicals, ions and radioactive material.

The term "enzyme substrate" is used throughout the specification to describe a substrate which will produce a fluorescent product upon modification.

The term "living organism" is used throughout the specification to describe an organism having an enzyme system that is capable of modifying the enzyme substrate of the present invention to produce a measurable fluorescent product. The term living organism includes active as well as dormant forms including encysted organisms.

The term "aquatic souce" is used throughout the specification to describe a water source that is to be measured. The term aquatic source includes all types of fresh and salt water supplies.

The term "$LC_{50}$" as used herein describes a concentration of toxicant which produces 50% lethality in test organisms.

The term "$EC_{50}$" as used herein describes a concentration of toxicant which produces a toxic affect and a measurable loss in the ability to of the tested organism to function, i.e., a loss in swimming ability, loss in reproductive ability, etc.

Numerous enzyme substrates may be used in the present invention and include any substrate which fluoresces after enyzmatic modification to produce a fluorescent product. Enzyme substrates containing any moiety which, when cleaved will result in a fluorescent product, may be used in the present invention. However, it has been found that the umbelliferyl group which produces umbelliferone is especially useful in embodiments of the present invention. Enzyme substrates having an umbelliferyl group for use in the present invention include, for example, 4-Methylumbelliferyl b-D-Galactoside, 4-Methylumbelliferyl a-D-Glucoside, 4-Methylumbelliferyl b-D-Xyloside, 4-Methylumbelliferyl acetate, 4-Methylumbelliferyl N-Acetyl-b-D-Galactosaminide, 4-Methylumbelliferyl N-Acetyl-a-D-Glucosaminide, 4-Methylumbelliferyl-b-D-Glucosaminide, 4-Methylumbelliferyl-a-L-Arabinofuranoside, 4-Methylumbelliferyl-a-L-Arabinoside, 4-Methylumbelliferyl Butyrate, 4-Methylumbelliferyl b-D-Cellobioside, 4-Methylumbelliferyl b-D-N,N'-Diacetyl-Chitobioside, 4-Methylumbelliferyl Elaidate, 4-Methylumbelliferyl b-D-Fucoside, 4-Methylumbelliferyl a-L-Fucoside, 4-Methylumbelliferyl b-L-Fucoside, 4-Methylumbelliferyl a-D-Galactoside, 4-Methylumbelliferyl b-D-Glucoside, 4-Methylumbelliferyl b-D-Glucuronide, 4-Methylumbelliferyl Heptanoate, 4-Methylumbelliferyl a-D-Mannopyranoside, 4-Methylumbelliferyl b-D-Mannopyranoside, 4-Methylumbelliferyl Oleate, 4-Methylumbelliferyl Palmitate, 4-Methylumbelliferyl Phosphate, 4-Methylumbelliferyl Propionate, 4-Methylumbelliferyl Stearate, 4-Methylumbelliferyl Sulfate, 4-Methylumbelliferyl b-D-N,N',N'''-Triacetyl Chitotriose, 4-Methylumbelliferyl 2,3,5-Tri-0-Benzoyl-a-L-Arabinofuranoside, among others.

The amount of enzyme substrate used in the present invention is that amount which produces a fluorescent product upon enzymatic modification. It has been found useful to include an amount of at least one enzyme substrate ranging from about 1 part per million (ppm) to about 100 parts per million. However, amounts outside these ranges may also be used.

The enzyme substrate may be presented directly in the test and reference samples or alternatively, may be sonicated, milled or otherwise physically modified before being used.

The bioassay of the present invention makes use of a living organism to cleave the fluoremetric markers from the enzyme substrate and produce a fluorescent product. These fluorescent markers are cleaved from the substrate as a function of the viability of the test specie's enzymatic system. Virtually any living organism having an enzyme system which can modify the fluorescent enzyme substrates to produce a fluorescent product may be used in the present invention. Typical enzymes or enzyme systems that may be useful for modifying the enzyme substrates to produce fluorescent products according to the present invention include, for example, AMP Deaminase, Aryl hydrocarbon Hydroxylase, 7-Ethoxycoumarin 0-Deethylase, Cytochrome P-450 (general activity), 7-Alkoxycoumarin 0-Dealkylase, 0-Deethylase and Adenylate Cyclase, among others.

Useful living organisms for use in the present invention include, for example, various bacteria, fungi, protozoans, Cnidaria, especially for example, Hydra, members of the phylum Platyhelminthes, such as Planarians, Nemertines, Aschelminthes, especially including rotifers, Brachiopods, such as *Ligoula spp.*, various molluscs, especially including snails, clams, squid and octupi after feeding enzyme substrate incorporated into composite feed, Polychaetes, especially including *Nereis spp.*, members of the phylum Arthropoda, especially including mysid shrimp, insect larvae and *Daphnia spp.* and various vertebrates, including fish such as fathead minnows, amphibians and other groups in various stages of their life cycles.

Especially useful organisms for use in the present invention include *Daphnia magna, Ceriodaphnia dubia, Daphnia pulex,* and species of mixed bacterial and microbial cultures from municipal sewage and industrial waste treatment plants, including *Nitrosomonas spp.* and *Nitrobacter spp.* In addition to the above living organisms, additional organisms that are especially useful in the bioassay of the present invention include those organisms whose bodies fluoresce after exposure to the fluorescent enzyme substrates. These organisms include, in addition to *Daphnia spp., Brachionus spp.* (rotifers), *Artemia salina* (brine shrimp), juvenile and adult *Pimephales promelas* (fathead minnows) and fruit fly larvae, among others.

The number of organisms that are used in the samples of the present invention ranges greatly depending upon the type of organism utilized. For example, in the case of bacteria and other microbes, the number of organisms will generally number in the millions, while in the case of multi-cellular organisms such as the Daphnia or fathead minnow, the number of organisms will generally be less than ten, preferably about 5 organisms.

In determining the amount of toxicant in an aquatic source, the sensitivity of the bioassay ranges from parts per hundred (effluent from a factory) to parts per trillion (such as measuring the amount of a particular ion or chemical compound such as 2,3,7,8-TCDD).

In general, in determining toxicant levels each sample, including reference standard, is run in triplicate. The tests are generally run for periods ranging from about 10 minutes to several hours depending upon the organism and enzyme substrate used and the toxicant measured.

Typical United States Environmental Protection Agency (EPA) aquatic toxicity protocols require an aquatic toxicologist to observe the lethal and sublethal effects of toxicants for predetermined time intervals (i.e., 0, 4, 8, 24, 72 and 96 hours). To perform the EPA protocol, the following steps are completed:

[a] develop a series of test concentrations of the aquatic source to be tested;

[b] assign the test organisms to each test concentration; and

[c] observe the test for lethal and sublethal affects at predetermined time intervals.

The bioassay of the present invention simplifies the task of observing lethal and sublethal effects of toxicants on living organisms. Rather than having to perform the test over a period or one, two, four or more days as in the case of the EPA test, the bioassay of the present invention allows the investigator to make an accurate determination of toxicant levels in periods of as little as several minutes and generally within an hour or two.

In addition to the above, the bioassay and the methodology of the present invention allows a determination of the general health of an aquatic population. This would have significant utility at a fish hatchery to determine the relative health of the fish population. The substrate could be delivered with feed or added directly to the water column in a hatchery. In addition, the present invention could be used to get a more complete picture of organism health, for example at a hatchery or in a water body. The toxicity test could also be used in a wastetreatment plant to gauge what would be an allowable (non-deleterious) rate of introduction of a known toxicant into a biologically activated waste treatment plant. In addition, the present invention could be utilized to guage the effectiveness of a waste water treatment plant's effectiveness.

The bioassay of the present invention may be used to measure concentrations of a large number of toxicants. Basically, any toxicant which exhibits a deleterious affect in a living organism may be measured accurately including, for example copper, cadmium, mercury, zinc, chromium, phenol, benzene, formaldehyde, toluene, other organics, including polychlorinated benzene, sodium polychlorinated phenols and various salts, including sulfides and other toxicants.

In the method of the present invention, the procedure for determining the effects of a toxicant in an aquatic source on living organisms includes the steps of:

1) preparing a test sample aquatic source, generally in triplicate;

2) preparing reference samples in triplicate, each triplicate set of reference samples containing an amount of toxicant ranging from 0 up to at least about the $LC_{50}$ or $EC_{50}$ concentration for said toxicant;

3) adding living organisms to the samples from steps 1 and 2 in amounts sufficient to produce a measurable fluorescent product from an enzyme substrate incubated with said organisms and allowing a period of incubation;

4) adding enzyme substrate to the samples from step 3 in quantities effective to produce a measurable fluorescent product and mixing the samples to produce uniformity;

5) allowing a further period of incubation at a temperature ranging from about 0° C. to about 30° C. for a period of at least about one minute; and 6) exposing the samples to an ultraviolet light source and measuring the fluorescent light emitted.

Additional steps useful in the method of the present invention include sonicating the substrate solution and calculating $LC_{50}$ values and $EC_{50}$ values using standard statistical methods. Alternatively, the Environmental Protection Agency (EPA) provides, on a regular basis, computer programs entitled "Movings Avergage", "Probit" or "Binomial" (available from the EPA), the general methodologies of which are readily known by those of ordinary skill in the art. The following examples are provided for purposes of illustrating the present invention only and are not to be taken as a limitation of the scope of the present invention.

EXAMPLE 1

Determination of an $EC_{50}$ Value in a Multiwell Plate

The objective of this example was to determine the $EC_{50}$ value and its confidence limits for the test substance copper sulfate ($CuO_4$) to the common water flea, *Daphnia magna*.

Using the invertebrate *Daphnia magna* as a test species a series of test concentratins are established with the standard reference toxicant copper sulfate, $CuSO_4$, in triplicate at the following concentrations:

| |
|---|
| 0-A ppm replicates 1, 2 and 3 |
| 0-B ppm replicates 1, 2 and 3 |
| 0.01 ppm replicates 1, 2 and 3 |

-continued

| |
|---|
| 0.1 ppm replicates 1, 2 and 3 |
| 1.0 ppm replicates 1, 2 and 3 |
| 10.0 ppm replicates 1, 2 and 3 |

One ml of each of the above $CuSO_4$ solutions was pippetted into a mutiwell plate (3 replications per concentration, 1 ml per replicate). To each of 18 wells in the plate 5 *Daphnia magna* were added and exposed to the test concentrations for a period of five minutes. Then to each of the 18 wells, with the exception of 0-B 1, 2 and 3, 1.0 mg of 4-Methylumbelliferyl b-D-Galactoside (MUF) was dropped onto the surface of each well. The powder settled to the bottom of each well. After 1 minute of exposure, each sample was read. An ultra-violet light (black light) was held over the multiwell in a dark room. The fluorescent intensity of Controls 0-A ppm (maximum intensity) and Controls 0-B ppm (minimum intensity) were utilized as baselines to compare the effects of test concentrations 0.01 through 10.0 ppm $CuSO_4$. The following results, set forth in Table 1, below were observed.

The $EC_{50}$ was determined to be 3.2 ppm.

TABLE 1

| Test Concentration | Replicates | | |
|---|---|---|---|
| | #1 | #2 | #3 |
| 0-A ppm $CuSO_4$ | f | f | f |
| | all alive | all alive | all alive |
| 0-B ppm $CuSO_4$ | f | f | f |
| | all alive | all alive | all alive |
| 0.01 ppm $CuSO_4$ | f | f | f |
| | all alive | all alive | all alive |
| 0.1 ppm $CuSO_4$ | f | f | f |
| | all alive | all alive | all alive |
| 1.0 ppm $CuSO_4$ | f | f | f |
| | all alive | all alive | all alive |
| 10.0 ppm $CuSO_4$ | nf | nf | nf |
| | all alive | all alive | all alive | f = fluorescing
nf = non-fluorescing

This test detected a sublethal adverse affect at 10.0 ppm $CuSO_4$ in less than 10 minutes.

EXAMPLE 2

Determination of the EC50 Value in Test Tubes

Using *Daphnia magna* as a test species a series of test concentrations of the standard reference toxicant $CuSO_4$ was established in triplicate. Each replicate consisted of 10 ml of test media in a 15 ml glass test tube. Five organisms were placed in each tube. The tubes were then maintained for a period of one hour at ambient room environmental conditions. At the end of one hour 0.4 mg of the substrate 4-Methylumbelliferyl b-D-galactoside (MUF) was added. Fifteen minutes after the addition of the MUF the test tubes were taken into a dark room. The control replicates were then observed under black light. A record was made of the number of strongly fluorescing *Daphnia magna* bodies. All bodies fluoresced strongly. These organisms were then compared to each of the other triplicate concentrations. The number of organisms that were fluorescing as strongly as the controls were recorded.

The data was then analyzed statistically by conventional methods (*Methods for Measuring the Acute Toxicity of Effluents to Freshwater and Marine Organisms (Third Edition) EPA/600/4-85/013*). Each organism not fluorescing as strongly as the controls was treated as dead when handling the data. From this procedure $EC_{50}$ for Cu with *Daphnia magna* was determined to be 0.23 ppm.

11 standard reference toxicants were then analyzed by the above method. The results of that analysis appear below in table 2.

TABLE 2

| Compound | Mean EC50 | Coefficient of Variation |
|---|---|---|
| Cu | 0.23 ppm | 17% |
| NaPCP | 1.0 | 8% |
| Cd | 0.41 | 11% |
| NaLS | 74.1 | 32% |
| Phenol | 37.1 | 19% |
| Zn | 4.3 | 11% |
| Cr | 3.7 | 7% |
| Benzene | 6.5 | 3% |
| Hg | 0.02 | 21% |
| Formaldehyde | 39.2 | 14.3% |
| Toluene | 6.3 | 14% |

Note: Three tests were conducted at different times for each toxicant.

When the preceding $EC_{50}$ values were correlated to historical *Daphnia magna* 48 hour LC50 values, there is an excellent correlation ($R^2$ 0.81 with a significance of 0.004). This data is set forth in FIG. 1. In the figure, the diagonal line represents the "line of equality". If all the data points were situated on the line it would mean that the $EC_{50}$ values determined according to the present invention were exactly equal to the $LC_{50}$ values taken from the literature. Values in FIG. 1 that fall below the "line of equality" indicate that the $LC_{50}$ test was more sensitive than the $EC_{50}$ values obtained by the present invention. Values in FIG. 1 that fall above the "line of equality" indicate that the present invention is a more sensitive test.

FIG. 2 compares *Daphnia magna* data obtained with the bioassay of the present invention with Microtox high and low EC50 pure compound values taken from the literature. Microtox is a test available from Microbics, Inc. California, U.S.A. In brief, the Microtox test procedure measures the light output of bioluminescent bacteria before and after they are challenged by a sample of unknown toxicity. The degree of light loss—an indication of metabolic inhibition in the test organism—indicates the degree of toxicity of the sample. In almost all cases the values obtained with the present invention was as sensitive or more sensitive than the literature results from the Microtox tests. In FIG. 2 each bar that extends above the "0" horizontal line (x axis) indicates that the present invention is "x" times more sensitive and for bars extending below the "0" line, the Microtox test is "x" times more sensitive. For example, the present invention was between 15 and 200 times more sensitive to $CuSO_4$ than was Microtox testing.

FIG. 3 compares *Daphnia magna* sensitivity with 96 hour $LC_{50}$ pure compound values taken from the literature for *Pimephales promelas* (fathead minnow). In most cases, the present invention was as sensitive or more sensitive than the fathead minnow test.

The above methodology has been performed successfully with several invertebrate species including *Daphnia magna*, *Daphnia pulex*, *Ceriodaphnia dubia*, *Artemia salina* and finfish species.

EXAMPLE 3

Determination of Toxicity of Wastestream to Activated Sludge

Treatment plants depend on biological activity in their activated sludge to degrade pollutants. If the biological life in the activated sludge is adversely affected by toxicants, it can no longer effectively degrade pollutants. Whenever a new or altered wastestream is taken into a plant the biological activity can be adversely affected. The following test is designed to address a wastestream's level of toxicity to the plant's biological community in the sludge.

A fluorometer (Sequoia-Turner Model 450, available from Sequoia-Turner, Calif., USA) was used to determine the intensity of fluorescence at each test concentration. A total of 21 20 ml test tubes with a test volume of 15 ml were established with the following proportions of activated sludge supernatant to test wastestream in triplicate:

| Supernatant | Test Wastestream |
|---|---|
| 100% a, b, c | 0% a, b, c |
| 50% a, b, c | 50% a, b, c |
| 25% a, b, c | 75% a, b, c |
| 12% a, b, c | 88% a, b, c |
| 6% a, b, c | 94% a, b, c |
| 3% a, b, c | 97% a, b, c |
| 1.5% a, b, c | 98.5% a, b, c |

After the test concentrations were mixed, they were allowed to stand for 10 minutes before adding 2 mg of 4-Methylumbelliferyl-b-D-galactoside (MUF) to each tube. Each test tube was then rolled between the palms and placed in a test tube rack. After waiting five minutes (test specific) for the MUF to be altered by the organisms, the intensity of emissions was determined by exciting the tubes in the fluorometer at 340 and 375 nanometers. First, fluorescent determinations were made of all the "a" tubes. Then, "b" tubes and finally the "c" tubes. An $EC_{50}$ value and its confidence limits were determined by conventional methods (See, for example, EPA/600/4-85/013, supra).

EXAMPLE 4

Determination of the Toxic Effect of Influent on Waste Treatment Sludge

This example was undertaken to determine the toxic effect of an influent to the biologically active sludge at a waste treatment plant as in Example 3.

In this Example, the following wastestream test concentrations were made in triplicate 15 ml test tubes with a test volume of 10 ml: 0, 50, 75 and 100% wastestreams. Each of the samples (0, 50 and 75) were diluted with autoclaved culture water. To each of the test tubes was pipetted 2 ml of a mixed base (MBL). The MBL contains the microbial population. The MBL was incubated for 1 hour at ambient room temperature. Thereafter, 0.4 mg of MUF was added and the test tubes were hand rolled to homogenize. The microbes were allowed to react with the MUF substrate for 15 minutes. At the end of 15 minutes the tubes were subsampled (3.0 ml) and fluorescence was determined by a fluorometer (Sequoia-Turner Model 450). The fluorescent output from the controls was used as a baseline to judge emissions from test concentrations. EC50 values were calculated by plotting percent adverse effect against the sample concentrations (EPA/600/4-85/013).

EXAMPLE 5

Determination of the LC50 Value and Prediction of the EC50 of a Plant Discharge

*Daphnia magna* was exposed to a series of effluent concentrations. Each triplicate 10 ml sample was pipetted into a 15 ml glass test tube. The following effluent test concentrations were assayed: 0% (controls), 6.25%, 12.5%, 25%, 50% and 100%. 5 *Daphnia magna* (±1 day in age) were added to each test tube. The test tubes were maintained at ambient room temperature for 1 hour. At one hour each tube was injected with 0.4 mg of sonicated MUF in 250 ul of distilled water.

The tubes were then maintained at room temperature for a further period of 15 minutes. After 15 minutes the series was assessed as in Example 2. From this data, $EC_{50}$ values were calculated and LC50 values were accurately predicted.

Several complex effluents were bioassayed with both conventional 48 hour $LC_{50}$ methodology and the bioassay of the present invention with *Daphnia magna*. The results, which are presented in FIG. 4, produced an excellent correlation ($R^2$ values ranged from 0.90 to 0.96). In FIG. 6, $EC_{50}$ and $LC_{50}$ values are expressed in percent effluent.

I claim:

1. An aquatic bioassay for determining the existence of toxicants in an aquatic source comprising:
   (a) at least one test sample comprising:
      i. an aquatic source to be tested;
      ii. an effective amount of an enzyme substrate selected from the group consisting of 4-Methylumbelliferyl b-D-Galactoside, 4-Methylumbelliferyl a-D-Glucoside, 4--Methylumbelliferyl b-D-Xyloside, 4-Methylumbelliferyl acetate, 4-Methylumbelliferyl N-Acetyl-b-D-Galactosaminide, 4-Methylumbelliferyl N-Acetyl-a-D-Glucosaminide, 4-Methylumbelliferyl-b-D-Glucosaminide, 4-Methylumbelliferyl-a-L-Arabinofuranoside, 4-Methylumbelliferyl-a-L-Arabinoside, 4-Methylumbelliferyl Butyrate, 4-Methylumbelliferyl b-D-Cellobioside, 4-Methylumbelliferyl b-D-N,N'-Diacetyl-Chitobioside, 4-Methylumbelliferyl Elaidate, 4-Methylumbelliferyl b-D-Fucoside, 4-Methylumbelliferyl a-L-Fucoside, 4-Methylumbelliferyl b-L-Fucoside, 4-Methylumbelliferyl a-D-Galactoside, 4-Methylumbelliferyl b-D-Glucoside, 4-Methylumbelliferyl b-D-Glucuronide 4-Methylumbelliferyl Heptanoate, 4-Methylumbelliferyl a-D-Mannopyranoside, 4-Methylumbelliferyl b-D-Mannopyranoside, 4-Methylumbelliferyl Oleate, 4-Methylumbelliferyl Palmitate, 4-Methylumbelliferyl Phosphate, 4-Methylumbelliferyl Propionate, 4-Methylumbelliferyl Stearate, 4-Methylumbelliferyl Sulfate, 4-Methylumbelliferyl b-D-N',N''-Triacetyl Chitotriose and 4-Methylumbelliferyl 2,3,5-Tri-O-Benzoyl-a-L-Arabinofuranoside; and
      iii. a number of multi-cellular organisms having bodies which fluoresce after metabolizing said enzyme substrate; and
   (b) reference standards, at least one of said reference standards comprising:
      i. an aquatic source containing a known toxicant concentration;
      ii. an identical amount and type of said enzyme substrate from (a)ii; and
      iii. an identical number and type of said living organism from (a)iii; and at least one additional reference standard comprising:
      i. an aquatic source containing an absence of toxicant;
      ii. an identical amount and type of said enzyme substrate from (a)ii; and
      iii. an identical number of organisms from (a)iii).

2. The bioassay according to claim 1 wherein said enzyme substrate is 4-Methylumbelliferyl-b-D-galactoside in a concentration of about 1 ppm to about 100 ppm.

3. The bioassay according to claim 1 wherein said bioassay contains at least three reference standards, each reference standard containing different concentrations of toxicant.

4. The bioassay according to claim 1 wherein said living organisms are selected from the group consisting of, multi-cellular fungi, Cnidaria, members of the phylum Platyhelminthes, molluscs, Polychaetes, members of the phylum Arthropoda, insect larvae, *Daphnia spp.*, juvenile and adult fathead minnows and amphibians.

5. The bioassay according to claim 1 wherein said living organisms are selected from the group consisting of *Daphnia magna, Ceriodaphnia dubia, Daphnia pulex, Daphnia spp., Brachionas spp.* (rotifers, *Artemia saline* (brine shrimp), juvenile and adult fathead minnows, mysid shrimp and fruit fly larvae.

6. The bioassay according to claim 1 wherein said living organisms are *Daphnia magna* and said enzyme substrate is 4-Methylumbelliferyl-b-D-galactoside.

7. A method of determining the toxicity of an aquatic source comprising:
   (1) preparing a test sample aquatic source;
   (2) preparing reference samples, each reference sample containing an amount of toxicant ranging form 0 up to at least about the $LC_{50}$ or $EC_{50}$ concentration for said toxicant;
   (3) adding to the samples from steps 1 and 2 a number of multi-cellular organisms having bodies which fluoresce after metabolizing an enzyme substrate selected from the group consisting of 4-Methylumbelliferyl b-D-Galactoside, 4-Methylumbelliferyl a-D-Glucoside, 4-Methylumbelliferyl b-D-Xyloside, 4-Methylumbelliferyl acetate, 4-Methylumbelliferyl N-Acetyl-b-D-Galactosaminide, 4-Methylumbelliferyl N-Acetyl-a-D-Glucosaminide, 4-Methylumbelliferyl-b-D-Glucosaminide, 4-Methylumbelliferyl-a-L-Arabinofuranoside, 4-Methylumbelliferyl-a-L-Arabinoside, 4-Methylumbelliferyl Butyrate, 4-Methylumbelliferyl b-D-Cellobioside, 4-Methylumbelliferyl b-D-N,N'-Diacetyl-Chitobioside, 4-Methylumbelliferyl Elaidate, 4-Methylumbelliferyl b-D-Fucoside, 4-Methylumbelliferyl a-L-Fucoside, 4-Methylumbelliferyl b-L-Fucoside, 4-Methylumbelliferyl a-D-Galactoside, 4-Methylumbelliferyl b-D-Glucoside, 4-Methylumbelliferyl b-D-Glucuronide, 4-Methylumbelliferyl Heptanoate, 4-Methylumbelliferyl a-D-Mannopyranoside, 4-Methylumbelliferyl b-D-Mannopyranoside, 4-Methylumbelliferyl Oleate, 4Methylumbelliferyl Palmitate, 4-Methylumbelliferyl Phosphate, 4-Methylumbelliferyl Propionate, 4-Methylumbelliferyl Stearate, 4-

Methylumbelliferyl Sulfate, 4-Methylumbelliferyl b-D-N,N',N''-Triacetyl Chitotriose and 4-Methylumbelliferyl 2,3,5-Tri-O-Benzoyl-a-L-Arabinofuranoside;

(4) adding an effective amount of said enzyme substrate to each of the sample from step 3 after incubation and mixing the sample to uniformity;

(5) incubating the sample from step 4 at a temperature of about 0° C. to about 30° C. for a period of at least one minute; and (6) exposing the samples from step 5 to an ultraviolet light source and measuring the fluorescent light emitted.

8. The method according to claim 7 wherein said enzyme substrate is 4-Methylumbelliferyl-b-D-galactoside.

9. The method according to claim 7 wherein said enzyme substrate is present in a concentration of about 1 ppm to about 100 ppm.

10. The method according to claim 7 wherein said living organisms are selected from the group consisting of multi-cellular fungi, Cnidaria, members of the phylum Platyhelminthes, molluscs, Polychaetes, members of the phylum Arthropoda, insect larvae, *Daphnia spp.*, fat head minnows and amphibians.

11. The method according to claim 7 wherein said living organisms are selected from the group consisting of *Daphnia magna, Ceriodaphnia dubia, Daphnia pulex, Daphnia spp., Brachionas spp.,* (rotifers) *Artemia saline* (brine shrimp), juvenile and adult fat head minnows, mysid shrimp and fruit fly larvae.

12. The method according to claim 7 wherein said living organism is *Daphnia magna* and said enzyme substrate is 4-Methylumbelliferyl-b-D-galactoside.

13. The method according to claim 7 wherein said measuring step is performed by a fluorometer.

14. The method according to claim 7 wherein said aquatic source is a hatchery and said method is used to determine the health of a fish population in said hatchery.

15. The method according to claim 7 wherein said aquatic source is a wastestream and said method is used to regulate the rate of introduction of said aquatic source containing said toxicant into a biologically activated waste treatment plant.

16. The method according to claim 7 wherein said aquatic source is treated water from a waste treatment plant and said method is used to guage the effectiveness of a waste water treatment plant.

17. A test kit for testing the toxicity of an aquatic source comprising:

(a) an enzyme substrate selected from the group consisting of 4-Methylumbelliferyl b-D-Galactoside, 4-Methylumbelliferyl a-D-Glucoside, 4-Methylumbelliferyl b-D-Xyloside, 4-Methylumbelliferyl acetate, 4-Methylumbelliferyl N-Acetyl-b-D-Galactosaminide, 4-Methylumbelliferyl N-Acetyl-a-D-Glucosaminide, 4-Methylumbelliferyl-b-D-Glucosaminide, 4-Methylumbelliferyl-a-L-Arabinofuranoside, 4-Methylumbelliferyl-a-L-Arabinoside, 4-Methylumbelliferyl Butyrate, 4-Methylumbelliferyl b-D-Cellobioside, 4-Methylumbelliferyl b-D-N,N'-Diacetyl-Chitobioside, 4-Methylumbelliferyl Elaidate, 4-Methylumbelliferyl b-D-Fucoside, 4-Methylumbelliferyl a-L-Fucoside, 4-Methylumbelliferyl b-L-Fucoside, 4-Methylumbelliferyl a-D-Galactoside, 4-Methylumbelliferyl b-D-Glucoside, 4-Methylumbelliferyl b-D-Glucuronide, 4-Methylumbelliferyl Heptanoate, 4-Methylumbelliferyl a-D-Mannopyranoside, 4-Methylumbelliferyl b-D-Mannopyranoside, 4-Methylumbelliferyl Oleate, 4-Methylumbelliferyl Palmitate, 4-Methylumbelliferyl Phosphate, 4-Methylumbelliferyl Propionate, 4-Methylumbelliferyl Stearate, 4-Methylumbelliferyl Sulfate, 4-Methylumbelliferyl b-D-N,N',N''-Triacetyl Chitotriose and 4-Methylumbelliferyl 2,3,5-Tri-O-Benzoyl-a-L-Arabinofuranoside in an amount sufficient to produce a final concentration of about 1 ppm to about 100 ppm in each of a test sample and several reference samples;

(b) a number of multi-cellular organisms having bodies which fluoresce after metabolizing said enzyme substrate; and (c) directions for using said enzyme substrate and said multi-cellular organism.

18. The kit according to claim 17 further comprising an exposure chamber.

19. The kit according to claim 17 further comprising a black (UV) light.

20. The kit according to claim 17 wherein said living organism is *Daphnia magna* and said enzyme substrate is 4-Methylumbelliferyl-b-D-galactoside.

* * * * *